(12) United States Patent  (10) Patent No.: US 8,332,045 B2
Sommer et al.  (45) Date of Patent: Dec. 11, 2012

(54) SYSTEM AND METHOD FOR CARDIAC LEAD SWITCHING

(75) Inventors: John Louis Sommer, Coon Rapids, MN (US); Michael William Kimmel, Edina, MN (US); Yong Kyun Cho, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 698 days.

(21) Appl. No.: 12/363,327

(22) Filed: Jan. 30, 2009

(65) Prior Publication Data

US 2009/0234405 A1 Sep. 17, 2009

Related U.S. Application Data

(60) Provisional application No. 61/035,950, filed on Mar. 12, 2008.

(51) Int. Cl.
*A61N 1/00* (2006.01)
(52) U.S. Cl. .................................................. 607/116
(58) Field of Classification Search .................. 607/115, 607/116, 122, 123
See application file for complete search history.

(56) References Cited

U.S. PATENT DOCUMENTS

| | | | |
|---|---|---|---|
| 6,101,417 A | 8/2000 | Vogel et al. | |
| 6,198,972 B1 | 3/2001 | Hartlaub et al. | |
| 6,871,091 B2 | 3/2005 | Wilkinson et al. | |
| 6,944,489 B2 | 9/2005 | Zeijlemaker et al. | |
| 6,985,775 B2 | 1/2006 | Reinke et al. | |
| 7,729,770 B2 | 6/2010 | Cabelka et al. | |
| 2004/0088012 A1 | 5/2004 | Kroll et al. | |
| 2007/0238975 A1 | 10/2007 | Zeijlemaker | |
| 2008/0269591 A1 | 10/2008 | Helperin et al. | |

OTHER PUBLICATIONS

PCT International Search Report, PCT/US2009/036462, 5 pgs.

*Primary Examiner* — Brian T Gedeon
(74) *Attorney, Agent, or Firm* — Stephen W. Bauer; Michael J. Ostrom (57) ABSTRACT

An implantable medical device (IMD) can include an implantable pulse generator (IPG), such as a cardiac pacemaker or an implantable cardioverter-defibrillator (ICD). Various portions of the IMD, such as a device body, a lead body, or a lead tip, can be provided to reduce or dissipate a current and heat induced by various external environmental factors. According to various embodiments, features can be incorporated into the lead body, the lead tip, or the IMD body to reduce the creation of an induced current, or dissipate the induced current and heat created due to an induced current in the lead.

25 Claims, 7 Drawing Sheets

SYSTEM AND METHOD FOR CARDIAC LEAD SWITCHING

CROSS-REFERENCE TO RELATED APPLICATION

This application claims the benefit of U.S. Provisional Application No. 61/035,950 filed Mar. 12, 2008.

FIELD

The present disclosure relates to implantable medical devices (IMDs), in particular to a system and method for use of a cardiac lead that includes a switch responsive to an external field, such as that generated during a magnetic resonance imaging (MRI) procedure.

BACKGROUND

The statements in this section merely provide background information related to the present disclosure and may not constitute prior art.

The human anatomy includes many types of tissue that can either voluntarily or involuntarily, perform certain functions. However, after disease or injury, certain tissues may no longer operate within general anatomical norms. For example, after disease, injury, age, or combinations thereof, the heart muscle may begin to experience certain failures or deficiencies. Some of these failures or deficiencies can be corrected or treated with implantable medical devices (IMDs). These devices can include implantable pulse generator (IPG) devices, pacemakers, implantable cardioverter-defibrillator (ICD) devices, cardiac resynchronization therapy defibrillator devices, or combinations thereof.

One of the main portions of the IMD can include a lead that is directly connected to tissue to be affected by the IMD. The lead can include a tip portion that is directly connected to the anatomical tissue, such as a muscle bundle, and a lead body that connects to the device body or therapeutic driving device. It is generally known that the device body or case portion can be implanted in a selected portion of the anatomical structure, such as in a chest or abdominal wall, and the lead can be inserted through various venous portions so that the tip portion can be positioned at the selected position near or in the muscle group.

The IMD generally remains with the patient during the rest of the patient's natural life. To that end, the IMD can be exposed to various environmental factors. For example, the patient may undergo a magnetic resonance imaging (MRI) procedure or other high frequency imaging procedures. In this case, portions of the IMD may act as an antenna and have current and thermal energy induced therein due to the MRI procedure. Accordingly, reduction or dissipation of the induced current or thermal energy may be useful in certain circumstances.

SUMMARY

An implantable medical device (IMD) can include implantable pulse generator (IPG) devices, implantable cardioverter-defibrillators (ICD), cardiac resynchronization therapy defibrillator devices, neurostimulators or combinations thereof. The IMD can be positioned in a selected portion of the anatomical structure, such as a chest wall or abdominal wall, and a lead can be positioned through a vein or transvenously so that a lead tip can be implanted in a portion of the cardiac or heart muscle. Various portions of the IMD, such as a case or device body, the lead body, or the lead tip, can be formed or augmented to reduce or dissipate heat production due to various external environmental factors. For example, a magnetic and/or electric field from a magnetic resonance imager (MRI), diathermy (including shortwave, microwave, ultrasound, or the like) or other energy field producing devices can induce currents in the lead. According to various embodiments, features or portions can be incorporated into the lead body, the lead tip, or the device body to reduce the creation of an induced current, or dissipate or increase the area of dissipation of thermal energy created due to an induced current in the lead.

An implantable medical device operable to provide therapy to an anatomical tissue is provided. The device can include a lead having a body. The body of the lead can have at least one conductor to transmit the therapy through the body of the lead. The device can further include at least one tip electrode coupled to the body of the lead. The at least one tip electrode can be in electrical communication with the at least one conductor to deliver the therapy to a first portion of the anatomical tissue in a first operational state. The device can also include at least one ring electrode fixedly coupled to the body of the lead. The at least one ring electrode can be in electrical communication with the at least one conductor to deliver the therapy to a second portion of the anatomical tissue in a second operational state. The lead can switch between the first operational state and the second operational state based on whether an external field is present.

In addition, an implantable medical device is also provided that includes a therapy device operable to generate the therapy for the anatomical tissue. The device can include a lead having a proximal end in electrical communication with the therapy device, a distal end and a body. The body of the lead can have at least one conductor to carry the therapy through the body of the lead. The device can further include at least one tip electrode coupled to the distal end of the lead that can be operable to deliver the therapy to a first portion of the anatomical tissue. The device can include at least one ring electrode coupled to the lead that can be operable to deliver the therapy to a second portion of the anatomical tissue. The device can also include a switch that can electrically couple the at least one conductor to the at least one tip electrode or to the at least one ring electrode. The device can include at least one control system that can activate the switch to electrically couple the at least one conductor to the at least one tip electrode in a first operational state or to electrically couple the at least one conductor to the at least one ring electrode in a second operational state based on an external field.

Further provided is a method of controlling a cardiac lead implanted in an anatomical structure during the presence of an external field. The method can include providing a lead having at least one conductor passing through the lead, at least one first electrode in electrical communication with the at least one conductor to deliver a therapy to a first portion of the anatomical tissue and at least one second electrode in electrical communication with the at least one conductor to deliver a therapy to a second portion of the anatomical tissue. The method can also include determining whether the external field is present and electrically coupling the at least one first electrode with the at least one conductor to deliver the therapy if the external field is absent. The method can include electrically coupling the at least one second electrode with the at least one conductor to deliver the therapy if the external field is present.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing a system and method for use of a cardiac lead that includes a switch that is responsive to an external field, such as that generated by a MRI. It should be noted, however, that the present teachings could be applicable to any appropriate procedure in which it is desirable to have a component that is responsive to external fields. Further, as used herein, the term module refers to an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality. Therefore, it will be understood that the following discussions are not intended to limit the scope of the appended claims.

Figure 1:
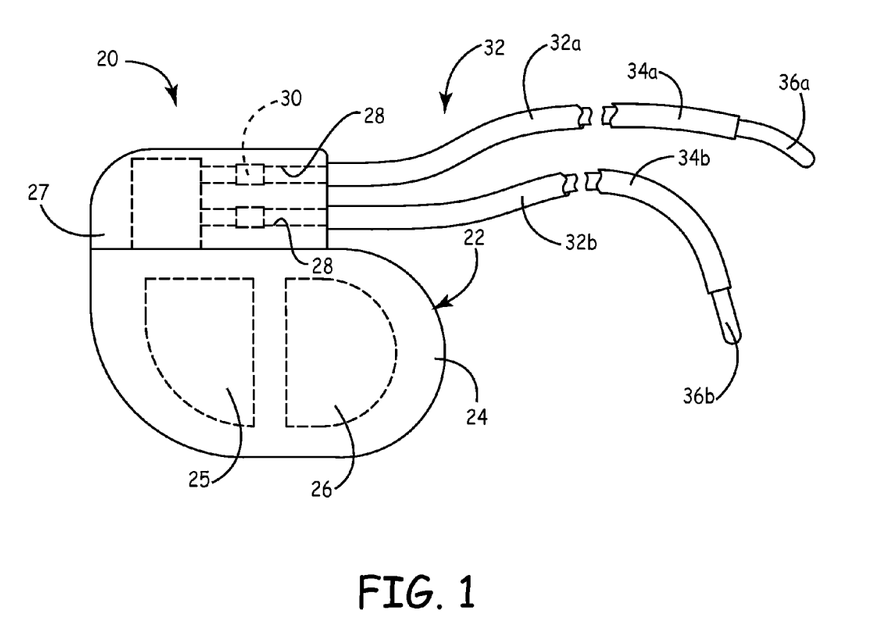
FIG. 1 is a view of an IMD including a lead connected to a device body.

With reference to FIG. 1, an implantable medical device (IMD) 20, which can include implantable pulse generator (IPG) devices, implantable cardioverter-defibrillator (ICD) devices, cardiac resynchronization therapy defibrillator devices, or combinations thereof, is exemplarily illustrated. The IMD 20 can include an implantable case or body assembly 22. The implantable case 22 can be formed of appropriate materials and include appropriate features, such as a hermetically sealed body wall 24. The body wall 24 can be made of a substantially inert material or of a conducting material.

Figure 2:
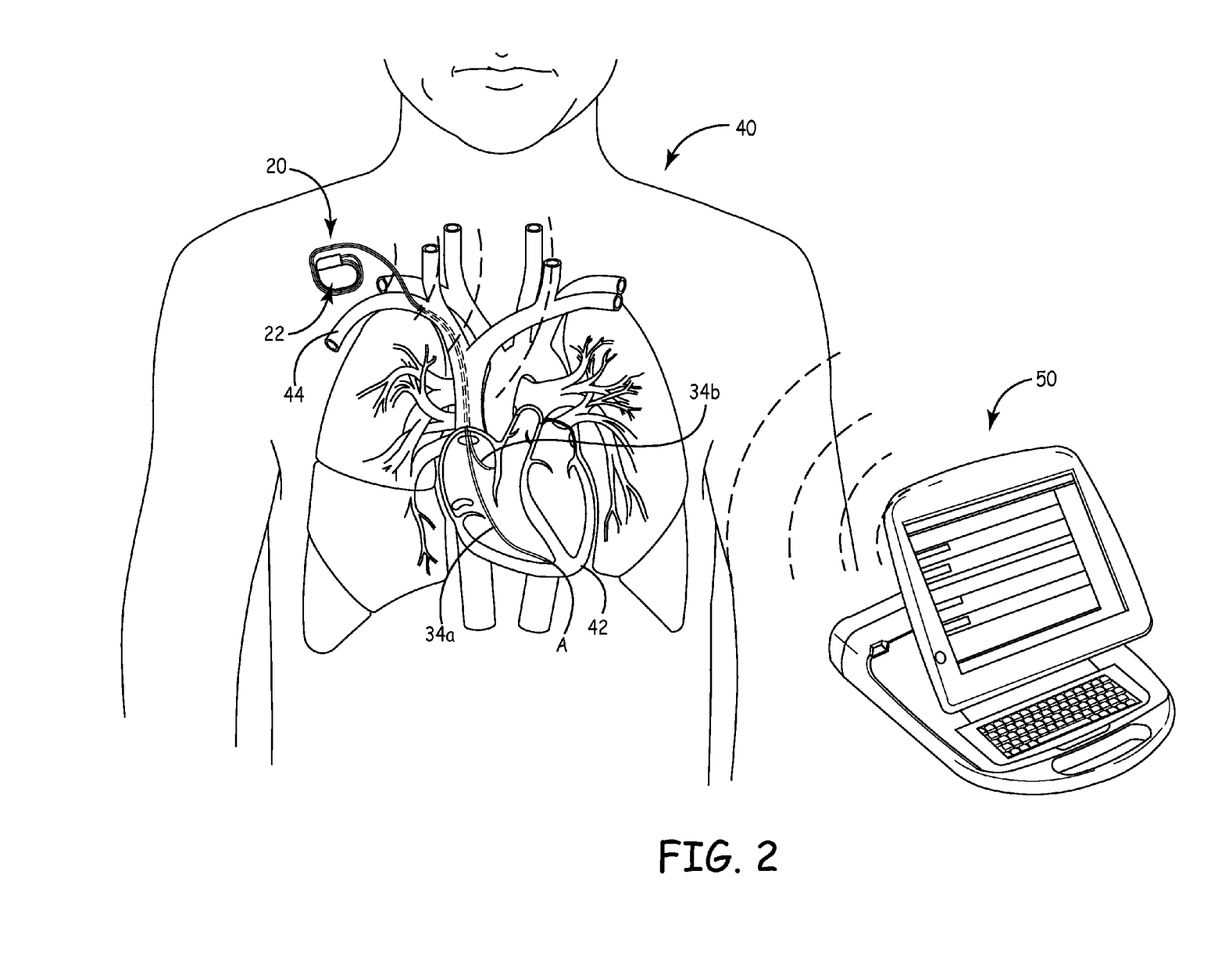
FIG. 2 is a simplified environmental view of the IMD implanted in a patient.

Contained within or associated with the case 22 can be a power device 25 (i.e., battery), a controller assembly 26, and a connector body 27. The controller assembly 26 can include a circuit board having a processor, memory, transmitter, receiver, and other appropriation portions, further discussed herein. The connector body 27 can extend from or be integrated with the case 22. The connector body 27 can include multiple ports 28 that each interconnect with a connector terminal 30 of a lead assembly 32. FIG. 1 illustrates two lead assemblies 32a, 32b where each lead assembly 32a, 32b includes lead bodies 34a, 34b extending from tip electrodes 36a, 36b. Although the IMD 20 is illustrated in FIGS. 1 and 2 as including two lead assemblies 32a, 32b, it will be understood that any number of lead assemblies 32 could be employed with the IMD 20 depending upon the malady of the patient and the particular IMD 20 employed. Moreover, the switch assembly further discussed herein can be associated with one or all of the lead assemblies 32a, 32b for the particular IMD 20 employed.

A fixation mechanism can also be included with each lead assembly 32a, 32b to affix each tip electrode 36a, 36b relative to or in a selected tissue of the patient. The fixation mechanism can be near each tip electrode 36a, 36b or define a portion of the tip electrode 36a, 36b. Fixation mechanisms can be any appropriate type, including a grapple mechanism, a helical mechanism, a drug-coated connection mechanism, and other appropriate connection mechanisms.

A majority of each lead body 34a, 34b can also be formed in a generally known and selected manner. For example, the various conductors and electrical components can be encased in silicone, polyurethane, and other appropriate materials. For example, at least one inner electrical conductor (identified as 150 in FIG. 4) can extend from each connector terminal 30 to engage each tip electrode 36a, 36b (identified as 142b in FIG. 4). It will be understood by one skilled in the art that the inner electrical conductor can be one piece or multiple components that are interconnected. Also, more than one inner electrical conductor can be provided, such as one inner electrical conductor for each electrode in each lead assembly 32a, 32b. The inner electrical conductor can also be cannulated or include a solid or non-cannulated cable. The casing material of each lead body 34a, 34b can electrically insulate the inner electrical conductor from an external environment.

The IMD 20, including the components discussed above, can be implanted in a patient 40 as illustrated in FIG. 2. The IMD 20 can include one or more lead assemblies 32, such as the first lead assembly 32a and the second lead assembly 32b. The first lead assembly 32a and the second lead assembly 32b can be connected to the connector body 27. As one skilled in the art will understand, the position of lead bodies 34a, 34b can depend upon the type of IMD and the malady of the patient 40. For example, the lead assemblies 32a, 32b can be positioned transvenously to positions within a heart 42 or on the outside of the heart 42. The IMD 20 can be provided to pace the heart 42, defibrillate the heart 42, sense conditions of the heart 42, etc.

The IMD 20, including the case 22 and the lead bodies 34a, 34b, can be implanted using known procedures. For example, an incision can be made in a chest wall or an abdomen wall of the patient 40 and the lead assemblies 32a, 32b can be passed through selected veins to selected portions of the heart 42 of the patient 40. The case 22 can also be positioned through the incision into a chest wall or abdominal wall of the patient 40. In a selected procedure, the leads assemblies 32a, 32b can be passed through a superior vena cava 44 of the patient 40. The lead tips or tip electrodes 36a, 36b can be positioned at various positions in the heart 42, such as at the ventricles or atriums thereof. The position of the lead assemblies 32a, 32b and tip electrodes 36a, 36b can be selected for pacing, defibrillation, sensing, or other appropriate procedures. The specific implantation procedure, position of the tip electrodes 36a, 36b, and the like can depend upon the patient 40, the surgeon performing the procedure, the specifics of the lead assemblies 32a, 32b, or other considerations.

As discussed above, the IMD 20, including the case 22 and the lead assemblies 32a, 32b can include various features or controls to defibrillate or pace the heart 42. The controls can include a processor associated with the controller assembly 26 located within the case 22. The processor can be programmed to control driving a current through the lead bodies 34a, 34b to the tip electrodes 36a, 36b to defibrillate or pace the heart 42.

With continued reference to FIG. 2, a programmer or programming system 50 can be provided. The programmer 50 can include a telemetry system that is operable to wirelessly transmit a signal to the processor within the case 22. It will be understood that a wired communication system can also be used. In addition, an induction system can be used where a coil is positioned near the case 22 and a signal is sent from the programmer 50 via induction. The programmer 50 can also receive information from the IMD 20 (e.g. tachycardia rhythms, times and programming settings) to assist in providing an appropriate program for therapy and to determine if the IMD 20 is operating properly. The programmer 50 can include any appropriate programming system, including one generally known to those skilled in the art, such as the Medtronic CARELINK™ programmer, sold by Medtronic, Inc. of Minneapolis, Minn.

Moreover, the IMD 20, including the case 22 and the lead assemblies 32a, 32b, can be formed to counteract or interact with various environmental factors. For example, the lead assemblies 32a, 32b can include features or portions to re-direct or dissipate thermal energy created by an induced current. Induced currents can be created due to an external field, such as an electromagnetic field acting on the conductors of the lead assemblies 32a, 32b.

For example, according to various embodiments, the patient 40 which has the implanted IMD 20 may receive a certain therapy or diagnostic technique, such as a magnetic resonance image (MRI) scan. Although not illustrated, a MRI, generally understood by one skilled in the art, uses high frequency radio frequency (RF) pulses and strong magnetic fields to create image data regarding the patient 40. Generally, a MRI will have a frequency of about 42 MHz per tesla. Many common MRI systems use about 1.5 tesla magnetic fields and have a corresponding RF frequency of about 63 MHz. Without being bound by the theory, the strong magnetic fields in a MRI can induce aligned spins of sub-atomic particles and the high frequency RF pulses can be used to change the alignment or otherwise affect the sub-atomic particles within the patient 40.

The strong magnetic fields and RF pulses may induce currents within the lead assemblies 32a, 32b of the IMD 20. The current induced in the lead assemblies 32a, 32b may cause certain affects, including heating, of the various lead components. According to various embodiments, such as those discussed herein, components, controls and/or mechanisms can be provided to reduce or eliminate the amount of current or thermal energy induced within each tip electrode 36a, 36b, or increase an area over which the current or thermal energy can be dissipated.

Figure 3:
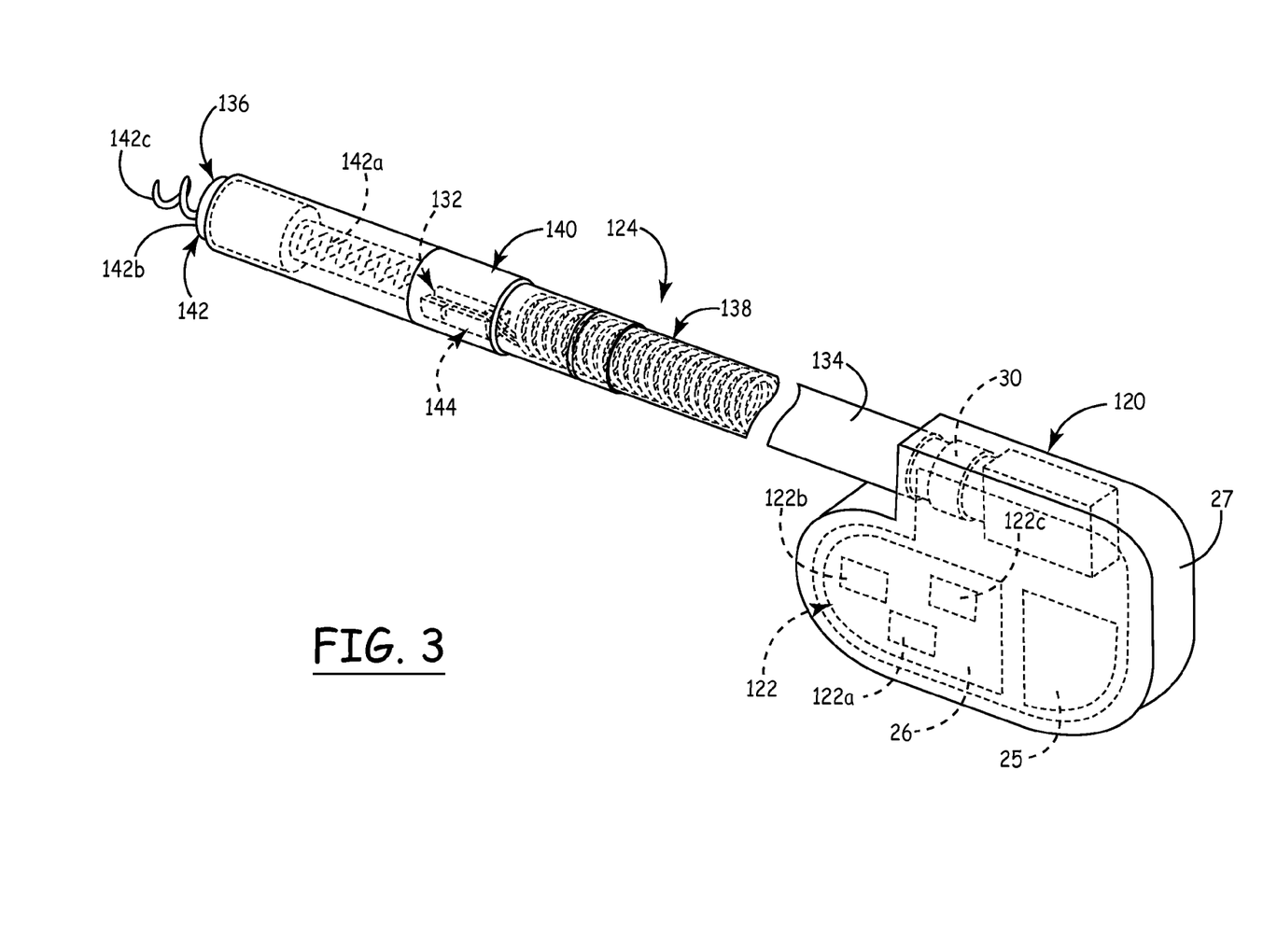
FIG. 3 is a simplified environmental view of an IPG that includes an exemplary cardiac lead system with a switch responsive to an external field, such as that generated during a magnetic resonance imaging (MRI) procedure.

According to various embodiments, and with reference to FIG. 3, in one example the IMD 20 can comprise an implantable cardiac device, such as an implantable pulse generator (IPG) 120. As the IPG 120 that will be described herein can be similar to the IMD 20 described with reference to FIGS. 1-2, similar reference numerals will be used to denote like components. It should be noted that, while the IPG 120 is illustrated herein as including one lead assembly, the IPG 120 can include any number of lead assemblies depending upon the malady of the patient 40. Moreover, each lead assembly can include a switch assembly, as further discussed herein. With continued reference to FIGS. 3-5, in one example, the IPG 120 can be used to generate electronic pulses to treat bradycardia, and thus, can deliver a therapy to a desired location within the heart 42. In addition, the IPG 120 can receive electrical pulses from the heart 42 to enable the IPG 120 to monitor the heart rhythm to determine if a therapy is needed. As the IPG 120 can comprise any suitable IPG, such as one selected from the ADAPTA™ family of IPGs available from Medtronic, Inc. of Minneapolis, Minn., only the modified or augmented portions of the IPG 120 will be discussed in great detail herein.

Figure 4:
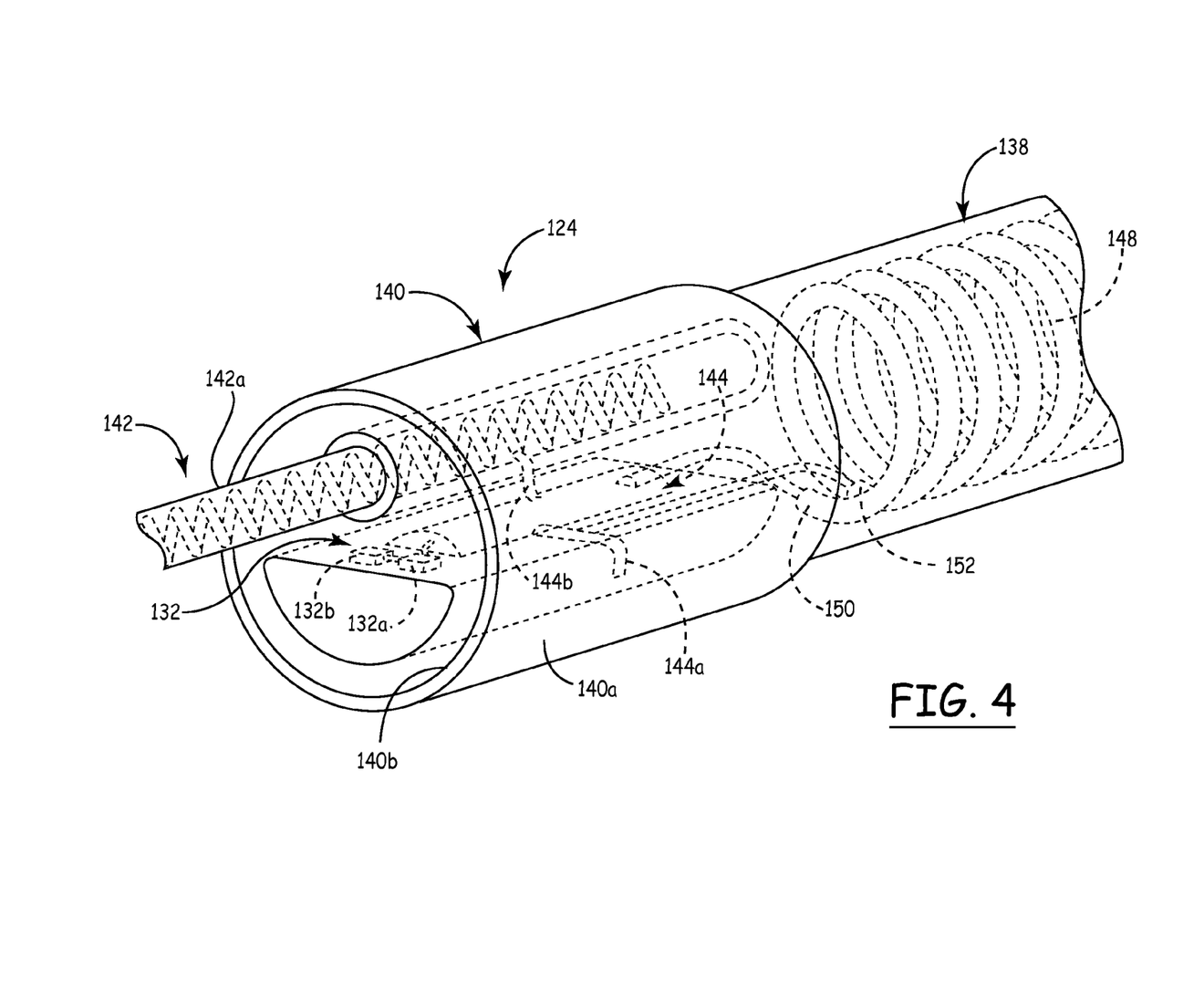
FIG. 4 is a simplified perspective view of a ring electrode and the switch of the cardiac lead system of FIG. 3.
Figure 5:
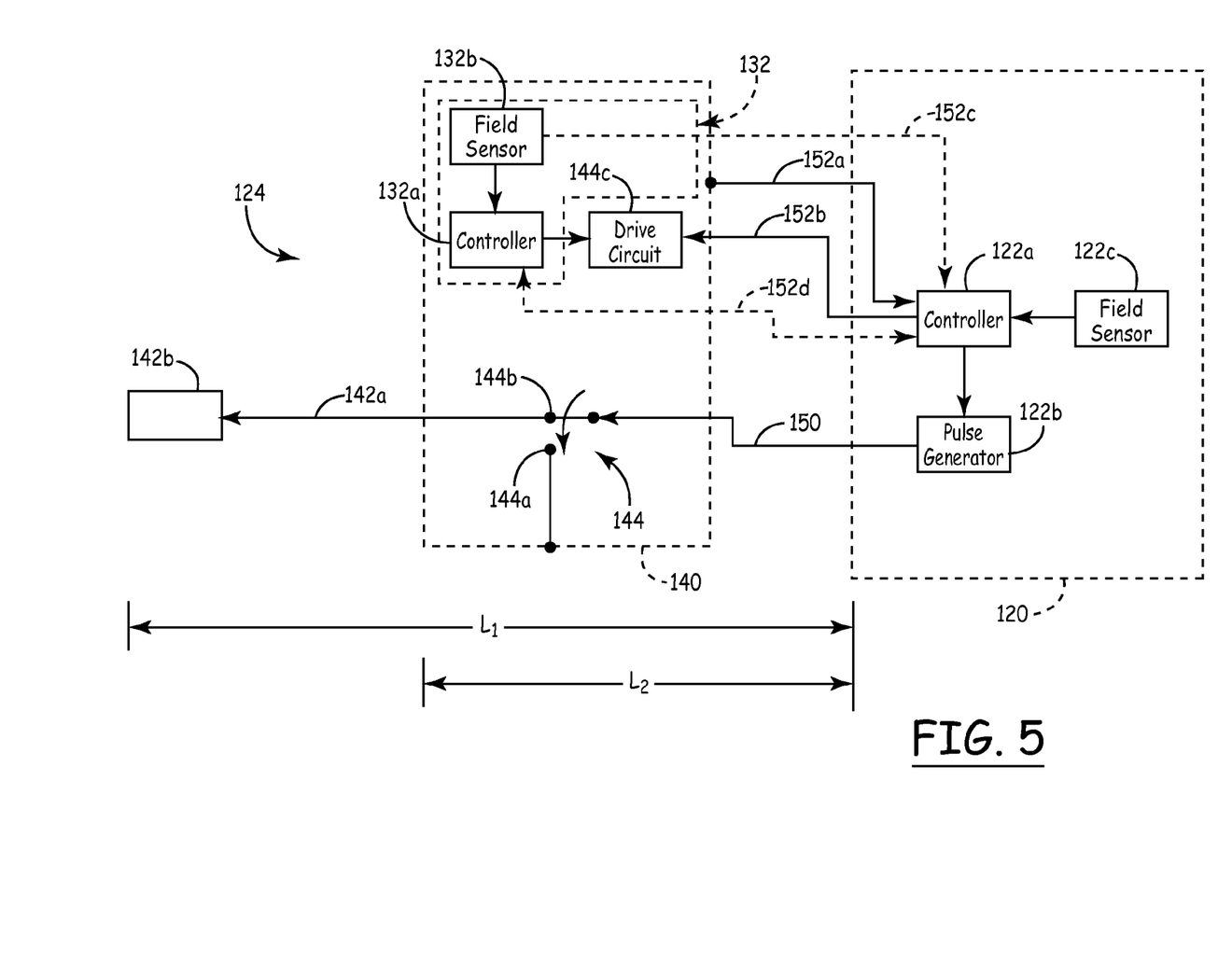
FIG. 5 is a simplified schematic illustration of the IPG and cardiac lead system of FIG. 3.

The IPG 120 can include a control system 122 and at least one IPG stimulation lead 124 which can be implanted into an anatomical structure, similar to the placement of the IMD 20 relative to the heart 42, as shown in FIG. 2. With reference to FIGS. 3-5, the control system 122 and the at least one IPG stimulation lead 124 can cooperate to reduce or eliminate the current or thermal energy induced in at least one tip electrode associated with the IPG stimulation lead 124, as will be discussed. The control system 122 can include a controller 122a, a pulse generator 122b and a field sensor 122c that form specific parts of the controller assembly 26, illustrated in the IMD 20 discussed with regard to FIGS. 1 and 2.

The controller 122a can be in communication with and responsive to the programmer 50 to receive a desired treatment plan for the heart 42, such as a desired voltage for the electrical stimulation of the heart 42. The controller 122a can also be in communication with the lead 124 to receive the sensed electrical activity of the heart 42, as will be discussed. The pulse generator 122b can be in communication with and responsive to the controller 122a to generate the desired therapy (i.e., electrical stimulation or pulse) for the heart 42. The pulse generator 122b can be in electrical communication with the lead 124 to supply the lead 124 with the desired therapy.

The field sensor 122c can be responsive to an external field, such as that generated by a MRI scan. In this regard, the field sensor 122c can be capable of detecting multi-level field strengths and/or can be capable of discriminating between different field ranges. For example, the field sensor 122c can comprise a Hall effect sensor or the magnetic field sensor 60 disclosed in commonly assigned U.S. Pat. No. 7,050,855, incorporated herein by reference. The field sensor 122c can also be an RF field sensor, as known in the art or can comprise another suitable field sensor used to detect an external field. The field sensor 122c can be in communication with the controller 122a to transmit a signal indicative of the surrounding field, such as whether the patient 40 is undergoing a MRI scan. Based on the signal received from the field sensor 122c, the controller 122a can adjust the voltage and location of the electrical therapy provided by the lead 124 to the heart 42, and optionally can also communicate the presence of the field to an optional field control system 132 of the lead 124, if employed, as will be discussed.

With reference to FIGS. 3-5, the lead 124 can both sense the electrical activity of the heart 42 and can also deliver electrical energy to pace the heart 42. The lead 124 can include a proximal end 134, a distal end 136, a body 138, at least one first or ring electrode 140, at least one second or tip electrode assembly 142, a switch assembly 144 and optionally, the field control system 132. As the proximal end 134, the distal end 136 and the body 138 of the lead 124 can comprise any suitable proximal end, distal end and body, such as that associated with the CAPSUREFIX™ line of cardiac leads available from Medtronic, Inc. of Minneapolis, Minn., only the modifications or augmentations to the proximal end 134, the distal end 136 and the body 138 of the lead 124 will be discussed in great detail herein. The proximal end 134 of the lead 124 can include a connector terminal 30 (FIG. 1) that can electrically couple the lead 124 to the connector body 27 of the IPG 120.

The distal end 136 can terminate within the anatomical structure adjacent to the desired location for the delivery of the therapy to the heart 42, as generally known, and illustrated in FIG. 2. As will be discussed, the ring electrode 140 and the tip electrode 142b can be coupled at or near the distal end 136 to deliver a therapy to an atrium A of the heart 42 (FIG. 2). It will be understood, however, that the ring electrode 140 and the tip electrode 142b can be coupled at any desired location along the body 138 of the lead 124. The body 138 of the lead 124 can extend from the proximal end 134 to the distal end 136. The body 138 of the lead 124 can comprise a bifilar coil 148. The bifilar coil 148 can include a pacing transmission member or pacing conductor 150 and at least one or multiple sensing/control transmission members or sensing/control conductors 152.

The pacing conductor 150 and the sensing/control conductor 152 can each be insulated to conduct or carry electrical signals along the body 138 of the lead 124. As best shown in FIG. 5, the pacing conductor 150 can be in communication with the pulse generator 122b to conduct or carry electrical pulses from the IPG 120 to the ring electrode 140 or the tip electrode assembly 142 to pace the heart 42. A first sensing/control conductor 152a can be in communication with the controller 122a of the IPG 120, and can conduct or carry electrical signals that indicate the electrical activity of the heart 42, as sensed by the ring electrode 140, as will be discussed. A second sensing/control conductor 152b can be in communication with the controller 122a and a drive circuit 144c of the switch assembly 144 to control activation of the switch assembly 144. A third sensing/control conductor 152c can be in communication with the field control system 132 of the lead to conduct or carry electrical signals to the controller 122a that can indicate the presence of an external field, as will be discussed. A fourth sensing/control conductor 152d can be in communication with the controller 122a of the IPG 120 and the optional field control system 132 to conduct or carry electrical signals between the control systems 122, 132.

The ring electrode 140 can be disposed near the distal end 136 of the lead 124 (FIG. 3). The ring electrode 140 can be generally annular, and can include an outer surface 140a and an inner surface 140b, as shown in FIG. 4. The outer surface 140a can be adjacent to the anatomical structure, such as the heart 42. The outer surface 140a of the ring electrode 140 can have a surface area that can range from about 0.5 square millimeters to about 40 square millimeters. Generally, the surface area of the ring electrode 140 can be about equal to or greater than a surface area of the tip electrode 142b. The outer surface 140a can enable the ring electrode 140 to sense the electrical activity of the heart 42, in a first operational state. In this regard, the control system 122 can be in communication with the ring electrode 140, via the first sensing/control conductor 152a to receive the sensed electrical activity of the heart 42. As will be discussed, based on the sensed electrical activity of the heart 42, the controller 122a of the IPG 120 can determine if a therapy is needed for the patient 40.

The inner surface 140b of the ring electrode 140 can be in electrical communication with the switch assembly 144 via a ring contact 144a. As will be discussed, the switch assembly 144 can electrically couple and carry the electrical pulses generated by the IPG 120 to the ring electrode 140 to enable the ring electrode 140 to deliver a therapy to the heart 42, in a second operational state, further discussed herein.

With reference to FIGS. 3-5, the tip electrode assembly 142 can also be in communication or electrically coupled with the switch assembly 144 to receive the electrical pulses from the IPG 120 in a first operational state. The tip electrode assembly 142 can include a transmission coil 142a, a tip electrode 142b and optionally, a fixation mechanism 142c. The transmission coil 142a and the tip electrode 142b can be in electrical communication with the switch assembly 144 to deliver the therapy to the anatomical tissue at a tip contact 144b. The tip electrode 142b can also have a surface area that can range from about 0.5 square millimeters to about 40 square millimeters, which can be smaller than the surface area of the ring electrode 140. The fixation mechanism 142c, if employed, can be used to secure the tip electrode assembly 142 to a desired location in the anatomical tissue, such as the heart 42, as illustrated in FIG. 2.

With reference to FIG. 4, in the first operational state, the transmission coil 142a can receive the therapy generated by the IPG 120 through the tip contact 144b of the switch assembly 144, and can conduct the therapy to the tip electrode 142b to deliver the therapy to the heart 42. In the second operational state, the transmission coil 142a can be electrically decoupled from the IPG 120 at the switch assembly 144 such that the transmission coil 142a does not receive any therapy generated by the IPG 120. Further, in the second operational state, the switch assembly 144 can electrically couple the pacing conductor 150 to the ring electrode 140 through the ring contact 144a, such that the ring electrode 140 can deliver the therapy generated by the IPG 120. This can reduce an amount of current or thermal energy that may be induced in the tip electrode assembly 142 by an external field, such as an external field generated by a MRI scan, since the tip electrode assembly 142 is essentially electronically decoupled from the lead 124 in the second operational state. As the tip electrode assembly 142 can be electrically decoupled from the lead 124, any current induced by the external field can be dissipated by the contact between the outer surface 140a of the ring electrode 140 and the anatomical structure. As the ring electrode 140 can have a larger surface area than the tip electrode 142b, the ring electrode 140 can distribute the effects of the induced current over a larger portion of the anatomical structure. Thus, the switch assembly 144 can thereby prevent induced currents from flowing to a smaller surface area electrode assembly, such as the tip electrode assembly 142.

With continued reference to FIGS. 3-5, the switch assembly 144 can be any suitable switch that is capable of electrically coupling the electrical pulses generated by the pulse generator 122b to either the ring electrode 140 or the tip electrode assembly 142, such as a transistor, a micro-electrical mechanical switch, etc. Illustrated schematically in FIGS. 4 and 5, the switch assembly 144 can include the ring contact 144a, the tip contact 144b and a drive circuit 144c. The ring contact 144a can electrically couple the switch assembly 144 to the ring electrode 140, via contact between the ring contact 144a and the inner surface 140b of the ring electrode 140, for example, which can thereby result in a unipolar pacing scheme. The tip contact 144b can electrically couple the switch assembly 144 to the tip electrode assembly 142, via contact between the tip contact 144b and the transmission coil 142a of the tip electrode assembly 142, which can thereby result in a bipolar pacing scheme. The drive circuit 144c can trigger or activate the switch assembly 144. The drive circuit 144c can comprise any suitable device capable of activating the switch assembly 144, such as a solenoid, as generally known in the art. The drive circuit 144c can be in communication with and responsive to the controller 122a and the optional field control system 132 to activate the switch assembly 144 to electrically couple either the ring electrode 140 or the tip electrode assembly 142 to the pacing conductor 150.

The optional field control system 132 includes a controller 132a and a field sensor 132b. As the field control system 132 can be optional, the controller 132a and field sensor 132b will be illustrated herein in phantom. If employed, the controller 132a can be in communication with and responsive to the controller 122a of the IPG 120 to receive a signal that indicates whether an external field is present, based on data received from the field sensor 122c.

Further, if employed, the controller 132a can be in communication with and responsive to the field sensor 132b, and can be in communication with the switch assembly 144. Based on the data received from the field sensor 132b, the controller 132a can transmit a signal to the controller 122a of the IPG 120, via the sensing/control conductor 152d, which can indicate that an external field is present. In addition, based on the data received from the field sensor 132b, and the controller 122a, the controller 132a can transmit a signal to the switch assembly 144 to electrically couple either the ring electrode 140 or the tip electrode assembly 142 to the pacing conductor 150 to receive the therapy from the IPG 120.

If employed, the field sensor 132b can be responsive to an external field, such as that generated by a MRI scan, and can be capable of detecting multi-level field strengths and/or can be capable of discriminating between different field ranges. Thus, if desired, the field sensor 132b can be substantially similar to the field sensor 122c.

With reference to FIG. 5, a schematic illustration of the IPG 120 including the lead 124 is shown. As discussed, the lead 124 can include the ring electrode 140 and the tip electrode 142b. The ring electrode 140 can have a surface area that is greater than the surface area of the tip electrode 142b, as discussed. The ring electrode 140 can further house the switch assembly 144. The pacing conductor 150 can carry a current from the pulse generator 122b to the switch assembly 144.

In one example, the switch assembly 144 can be activated by the IPG 120. In this regard, based on only the receipt of the signal from the field sensor 122c, the controller 122a can determine if the external field is present. If the external field is present, then the controller 122a can output a signal for the pulse generator 122b that sets the therapy to a high voltage pacing therapy and can output a signal for the drive circuit 144c to activate the switch assembly 144 to switch from the first operational state to the second operational state.

In another example, the switch assembly 144 can be activated by the IPG 120 and the field sensor 132b. In this regard, based on the receipt of the signal from the field sensor 122c and the signal from the field sensor 132b, the controller 122a can determine if the external field is present. If the external field is present, then the controller 122a can output a signal for the pulse generator 122b that sets the therapy to a high voltage pacing therapy and can output a signal for the drive circuit 144c to activate the switch assembly 144 to switch from the first operational state to the second operational state. The controller 122a can also determine if the signal from the field sensor 122c and the signal from the field sensor 132b are about equal. If the signal from the field sensor 122c and the signal from the field sensor 132b are not about equal, then the controller 122a can output error data for the programmer 50 that can indicate that one of the field sensor 122c and field sensor 132b has failed.

In another example, the switch assembly 144 can be activated by the control system 122 of the IPG 120 and the field control system 132 of the lead 124. In this regard, based on the signal from the field sensor 122c, the controller 122a can output a signal for the controller 132a that can indicate if an external field is present. If the external field is present, then the controller 132a can output a signal for the pulse generator 122b that sets the therapy to a high voltage pacing therapy. The field controller 132a can receive the signal from the controller 122a that indicates if the external field is present, and can receive the signal from the field sensor 132b that indicates if the external field is present. The controller 132a can determine if the signal from the field sensor 122c and the signal from the field sensor 132b are about equal. If the signal from the field sensor 122c and the signal from the field sensor 132b are not about equal, then the controller 132a can output a signal for the controller 122a such that the controller 122a can output error data for the programmer 50. If, based on at least one of the signal from the field sensor 122c and the field sensor 132b, the external field is present, then the controller 132a can also output a signal for the drive circuit 144c to activate the switch assembly 144 to electrically couple the ring electrode 140 to the IPG 120 in the second operational state.

If the lead 124 is not in the presence of an external field or in a normal operating state, then the switch assembly 144 can be in contact with the tip contact 144b, such that the current from the IPG 120 can flow to the tip electrode 142b, via the transmission coil 142a, in the first operational state. If the lead 124 is in the presence of the external field, then the switch assembly 144 can be in contact with the ring contact 144a to electrically couple the ring electrode 140 to the IPG 120, in the second operational state. Thus, in the presence of an external field, the tip electrode 142b can be electrically decoupled from the lead 124, which thereby reduces the effective length of the lead 124. In this regard, the amount of current or thermal energy induced in the lead 124 can depend upon a length of the lead 124. In the normal operating state, the length of the lead 124 can be illustrated as L1, while in the MRI operating state, the length L2 of the lead 124 can be illustrated as L2, since the tip electrode 142b is electrically decoupled from the lead 124. Thus, by electrically decoupling the tip electrode 142b from the lead 124, the overall conductive length of the lead 124 is reduced and the amount of current or thermal energy induced in the lead 124 can be greatly reduced, as well as reducing or eliminating heating of the tip electrode 142b.

Figure 6:
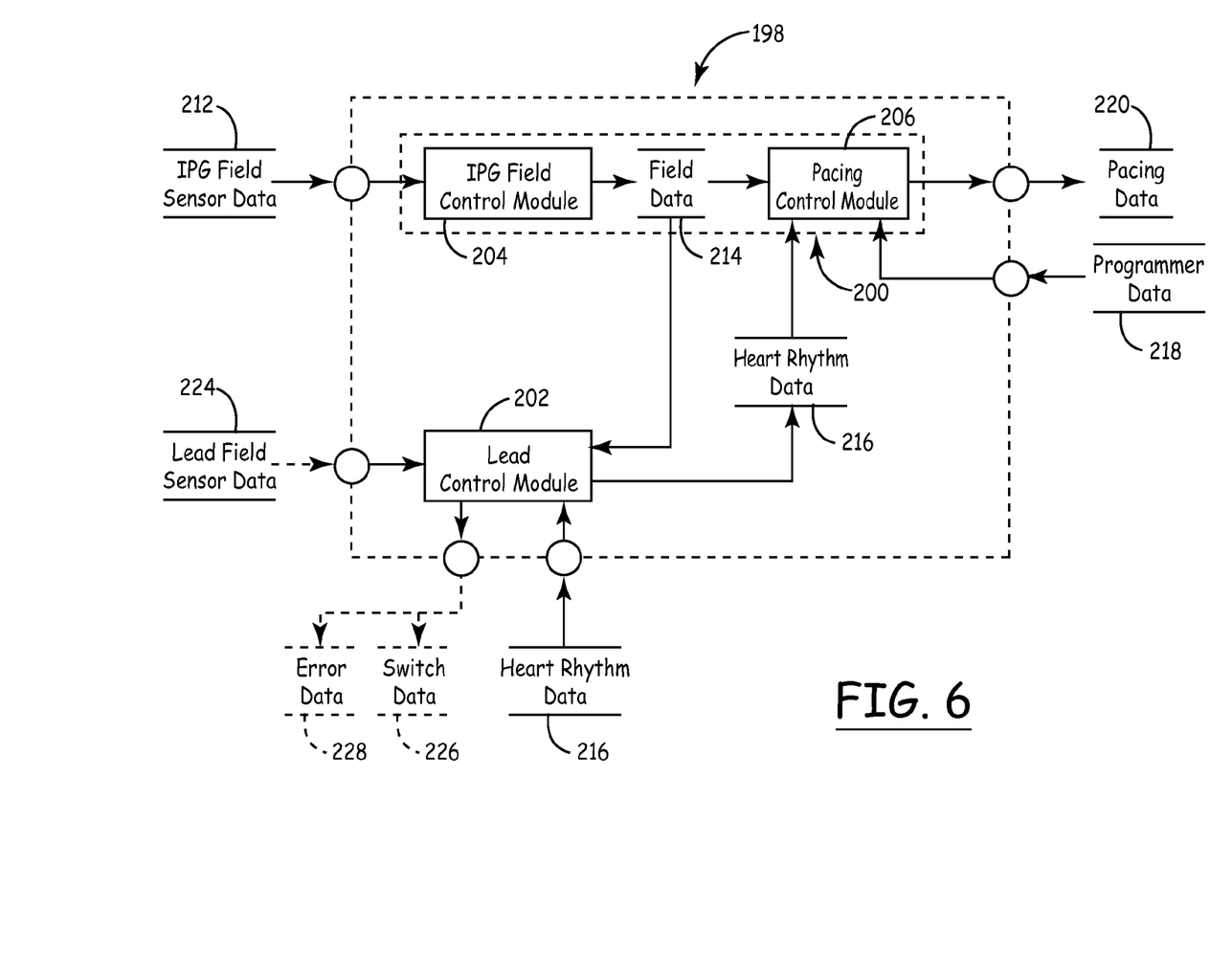
FIG. 6 is a dataflow diagram illustrating a control system performed by the IPG.

With reference now to FIG. 6, a dataflow diagram illustrates an exemplary control system 198 that can be embedded within the controller 122a of the IPG 120 and/or the controller 132a of the lead 124. Various embodiments of the control system 198 according to the present disclosure can include any number of sub-modules embedded within the controller 122a of the IPG 120 and/or the controller 132a of the lead 124. The sub-modules shown may be combined and/or further partitioned to similarly deliver a therapy to an anatomical tissue, such as the heart 42, in the presence of an external field, such as that encountered during a MRI scan. Inputs to the system can be received from the field sensors 122c, 132b, or even received from other control modules within the IPG 120, and/or determined by other sub-modules within the controller 122a of the IPG 120 and/or the controller 132a of the lead 124. In various embodiments, the control system 198 includes the controller 122a of the IPG 120 that can implement an IPG control module 200 and the controller 132a of the lead 124 that can implement a lead control module 202. It should be noted that although the IPG control module 200 can be implemented by the controller 122a of the IPG 120 and the lead control module 202 can be implemented by the optional controller 132a of the lead 124, both of the IPG control module 200 and the lead control module 202 can be implemented by the controller 122a of the IPG 120, if desired. With continued reference to FIG. 6, the IPG control module 200 can include an IPG field control module 204 and a pacing control module 206.

The IPG field control module 204 can receive as input IPG field sensor data 212. The IPG field sensor data 212 can comprise a signal from the field sensor 122c and optionally, the field sensor 132b if employed, that can be used to determine whether or not an external field is present. Based on the IPG field sensor data 212, the IPG field control module 204 sets field data 214 for the pacing control module 206 and the lead control module 202. The field data 214 can comprise data that indicates whether an external field, such as that generated by a MRI scan, is present.

The pacing control module 206 can receive as input the field data 214, heart rhythm data 216 and programmer data 218. The heart rhythm data 216 can comprise the electrical activity of the anatomical tissue, such as the heart 42, as sensed by the ring electrode 140. The programmer data 218 can comprise data received from the programmer 50, such as a desired therapy to be output by the IPG 120 based on the presence of an external field, such as that generated by a MRI scan. In one example, the programmer data 218 can comprise data that instructs the IPG 120 to output a pacing therapy at a high voltage, such as a voltage between about 5 volts (V) or about 10 volts (V), if the therapy is to be delivered by the ring electrode 140. In another example, the programmer data 218 can comprise data that instructs the IPG 120 to output a pacing therapy at a low voltage, such as a voltage between about 0.01 volts (V) or about 4.99 volts (V), if the therapy is to be delivered by the tip electrode assembly 142.

Generally, an operator can program the IPG 120, via the programmer 50, to output a high voltage pacing therapy when the patient 40 is about to undergo a MRI scan, and can instruct the IPG 120 to output a low voltage pacing therapy when the patient 40 has completed the MRI scan. During the MRI scan, a high voltage pacing therapy can be required as the ring electrode 140 delivers the pacing therapy to the heart 42. In this regard, as the ring electrode 140 can be spaced a distance from the distal end 136 of the lead 124, a higher voltage can be required to ensure that the pacing therapy reaches the desired portion of heart 42 (i.e. the tissue of the heart 42 adjacent to the tip electrode 142b). Upon exiting the MRI scan, the programmer 50 can program the return of the pacing therapy to a lower voltage, as on completion of the MRI scan, the switch assembly 144 can couple the tip electrode 142b to the IPG 120 to deliver the pacing therapy to the anatomical tissue.

Based on the field data 214, the heart rhythm data 216 and the programmer data 218, the pacing control module 206 outputs pacing data 220. The pacing data 220 comprises a desired therapy for the anatomical tissue, such as a desired electrical pulse to stimulate the heart 42. Thus, if based on the heart rhythm data 216, the pacing control module 206 determines that the heart 42 requires a pacing therapy, then, based on whether the patient 40 is undergoing a MRI scan, as indicated by the field data 214 and/or the programmer data 218, the pacing control module 206 outputs the appropriate level of therapy as pacing data 220. The pacing data 220 can instruct the pulse generator 122c to generate the desired therapy for the anatomical tissue.

The lead control module 202 can receive as input lead field sensor data 224, heart rhythm data 216 and field data 214. The lead field sensor data 224 can be optional, and can comprise a signal from the field sensor 132b that can be used to determine whether or not an external field is present, such as that generated during a MRI scan. Based on the lead field sensor data 224, heart rhythm data 216 and field data 214, the lead control module 202 can output switch data 226 and, optionally, error data 228. The switch data 226 can comprise a signal to the switch assembly 144 to drive the drive circuit 144c to electrically couple either the ring electrode 140 or the tip electrode assembly 142 to the pacing conductor 150 based on whether an external field is present. If it is determined that an external field is present, based on the lead field sensor data 224 and/or field data 214, then the switch data 226 can comprise a signal to electrically couple the ring electrode 140 to the pacing conductor 150 to receive the pacing therapy from the IPG 120. If it is determined that an external field is not present, then the switch data 226 can comprise a signal to electrically couple the tip electrode assembly 142 to the pacing conductor 150.

The error data 228 can comprise a signal transmitted to the programmer 50 that there is an error associated with either the field sensor 122c of the IPG 120 or the field sensor 132b of the lead 124, if employed. In this regard, if the field data 214 does not match the lead field sensor data 224, the lead control module 202 can output the error data 228 to indicate that there is a problem with either the field sensor 122c of the IPG 120 or the field sensor 132b of the lead 124.

Figure 7:
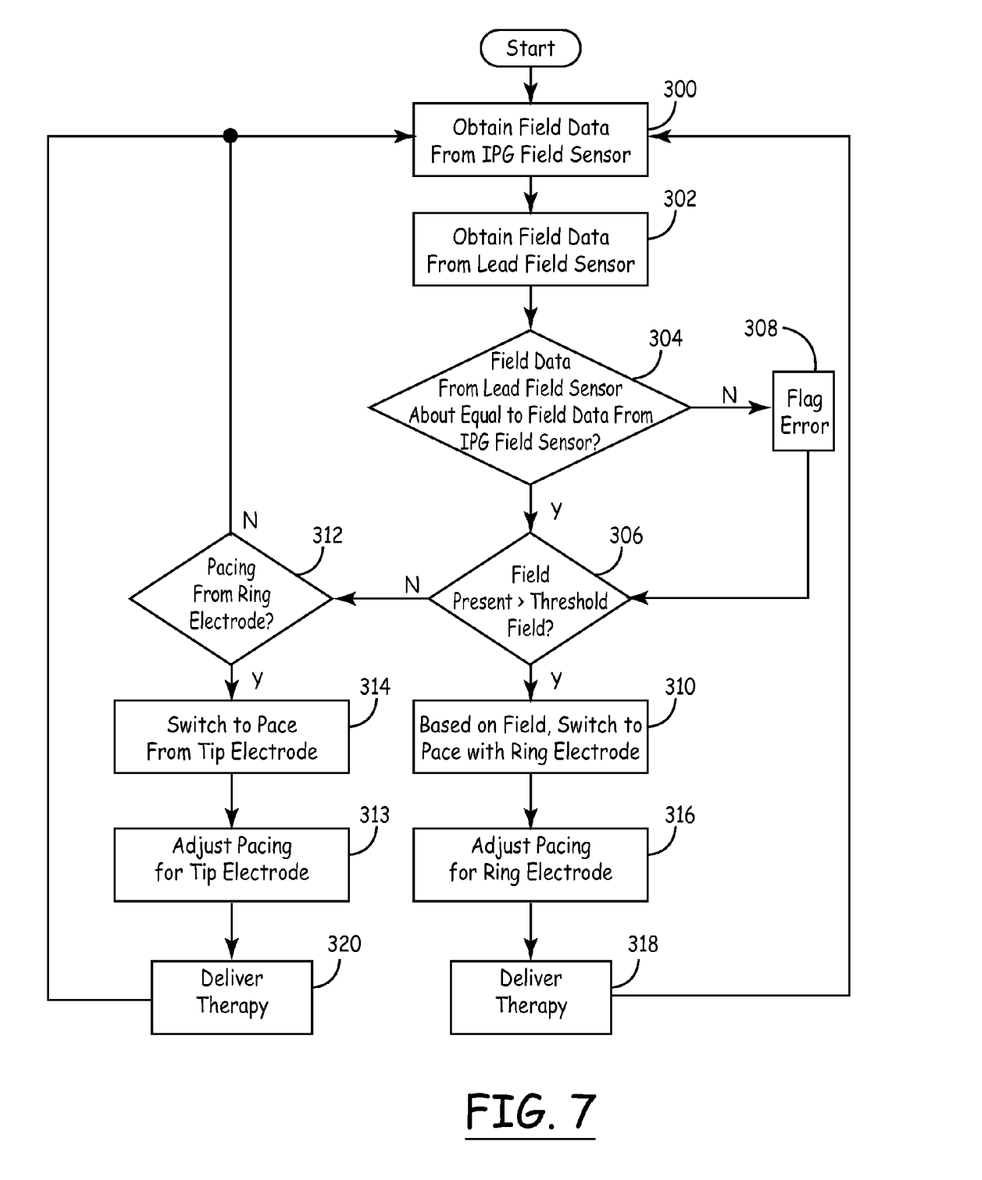
FIG. 7 is a flowchart illustrating an exemplary method performed by the IPG.

With reference now to FIG. 7, a process flow diagram illustrates an exemplary method that can be performed by the control system 198. At block 300, the method can obtain the IPG field sensor data 212 from the field sensor 122c of the IPG 120. Then, at block 302, the method can obtain the lead field sensor data 224 from the field sensor 132b of the lead 124, if employed. At decision block 304, the method can determine if the lead field sensor data 224 from the field sensor 132b is about equal to the IPG field sensor data 212 from the field sensor 122c. If the IPG field sensor data 212 and the lead field sensor data 224 measured by the respective field sensors 122c, 132b can be substantially equal, then the method goes to decision block 306. Otherwise, the method can output error data 228 at block 308 and then go to decision block 306.

At decision block 306, the method determines if the field present is greater than a threshold field. The threshold field can be equivalent to a field generated during a MRI procedure, and thus, can comprise a threshold value for a magnetic field or a threshold value for an electrical field. Further, the threshold field can be a value programmed into the IPG 120 by the programmer 50. If the field present is greater than the threshold field, then the method can go to block 310. Otherwise, the method can go to decision block 312.

At decision block 312, the method can determine if the ring electrode 140 of the lead 124 is delivering the desired therapy to the heart 42. If the ring electrode 140 is delivering the desired therapy, such as a pacing therapy, then the method goes to block 314. Otherwise, the method can loop to block 300.

At block 314, the method can activate the switch assembly 144 to electrically couple the IPG 120 to the tip electrode assembly 142 such that the tip electrode assembly 142 can deliver the desired therapy to the heart 42. Then, at block 313, the method can adjust the therapy to correspond with the tip electrode assembly 142. For example, the method can adjust the pacing data 220 to deliver a lower voltage to the anatomical tissue as the tip electrode assembly 142 can be adjacent to the desired target site in the heart 42, and thus, a smaller voltage can be used when delivering a therapy from the tip electrode assembly 142. Then, at block 318, the method can deliver the therapy to the anatomical tissue, if the controller 122a of the IPG 120 determines a therapy is necessary. The method can then loop to block 300.

At block 310, based on the field, the method can activate the switch assembly 144 to use the ring electrode 140 to deliver the pacing therapy to the heart 42. Then, at block 316, the method can adjust the pacing voltage so that the pacing therapy delivered by the ring electrode 140 reaches the desired portion of the heart 42. In this regard, the method can adjust the pacing voltage to a higher voltage to compensate for the distance between the ring electrode 140 and the distal end 136 of the lead 124. At block 320, the method can deliver the therapy to the anatomical tissue, if the controller 122a of the IPG 120 determines a therapy is necessary. Then, the method goes to block 300.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. An implantable medical device operable to provide a therapy to an anatomical tissue comprising:
    a lead having a body having at least one conductor to transmit the therapy through the body of the lead;
    at least one tip electrode coupled to the body of the lead, the at least one tip electrode in electrical communication with the at least one conductor to deliver the therapy to a first portion of the anatomical tissue in a first operational state;
    at least one ring electrode fixedly coupled to the body of the lead and in electrical communication with the at least one conductor to deliver the therapy to a second portion of the anatomical tissue in a second operational state; and
    wherein the lead switches between the first operational state and the second operational state based on whether an external field is present.

2. The device of claim 1, wherein the external field comprises a magnetic or electric field generated during a magnetic resonance imaging (MRI) scan.

3. The device of claim 2, further comprising:
    a control system operable to sense the presence of the external field; and
    a switch in communication with and responsive to the control system, the switch in electrical communication with the at least one conductor, the at least one tip electrode and the at least one ring electrode and operable to electrically couple the at least one conductor to either the at least one ring electrode or the at least one tip electrode based on a signal from the control system.

4. The device of claim 3, further comprising:
    a therapy device implanted in a portion of the anatomical tissue and operable to generate the therapy for the anatomical tissue, the therapy device in electrical communication with the at least one conductor to deliver the therapy to either the at least one tip electrode or the at least one ring electrode depending upon whether the lead is in the first operational state or the second operational state.

5. The device of claim 4, wherein the therapy device is an implantable pulse generator (IPG) and the lead is an IPG stimulation lead.

6. The device of claim 4, wherein the at least one conductor further comprises:
    a pacing conductor that receives the therapy from the therapy device and delivers the therapy to either the at least one tip electrode or the at least one ring electrode depending upon the first operational state or the second operational state; and
    a sensing conductor in electrical communication with the at least one ring electrode to receive a signal indicative of electrical activity at the second portion of the anatomical tissue and in electrical communication with the therapy device to conduct the signal to the therapy device.

7. The device of claim 6, wherein each of the at least one tip electrode further comprises:
    a transmission member in electrical communication with the switch and operable to receive the therapy from the pacing conductor; and
    an electrode in electrical communication with the transmission member to conduct the therapy to the first portion of the anatomical tissue adjacent to the electrode.

8. The device of claim 7, wherein the control system further comprises:
    at least one sensor responsive to the external field to generate a signal; and
    at least one controller in communication with the at least one sensor to receive the signal and in electrical communication with the switch to activate the switch such that the switch electrically couples the pacing conductor to either the at least one ring electrode or the at least one tip electrode based on the signal from the at least one sensor.

9. The device of claim 4, wherein the therapy device delivers the therapy at a first voltage if the therapy device is in electrical communication with the at least one tip electrode and delivers the therapy at a second voltage if the therapy device is in electrical communication with the at least one ring electrode, the second voltage being greater than the first voltage.

10. The device of claim 4, further comprising:
    a programmer operable to program the therapy device to deliver the therapy through the lead.

11. The device of claim 8, wherein the at least one sensor further comprises:
    a first sensor disposed in the therapy device and responsive to the external field to generate a first signal;
    a second sensor disposed in the lead and responsive to the external field to generate a second signal; and
    wherein the at least one controller receives the first signal and second signal and based on the first signal and second signal determines if the external field is present and outputs error data if the first signal is not about equal to the second signal.

12. The device of claim 11, wherein the at least one controller further comprises:
    a first controller disposed in the therapy device and in communication with at least the first sensor to receive the first signal and to generate the therapy; and
    a second controller disposed in the lead and in communication with the second sensor to receive the second signal and in communication the first controller to receive the first signal, the second controller operable to activate the switch based on the first signal, the second signal or a combination thereof.

13. The device of claim 1, wherein the at least one ring electrode has a surface area that is about equal to or greater than a surface area of the at least one tip electrode.

14. An implantable medical device operable to provide a therapy to an anatomical tissue comprising:
   a therapy device implanted in a portion of an anatomical structure and operable to generate the therapy for the anatomical tissue;
   a lead having a proximal end in electrical communication with the therapy device to receive the therapy, a distal end and a body having at least one conductor to carry the therapy through the body of the lead;
   at least one tip electrode coupled to the distal end of the lead that is operable to deliver the therapy to a first portion of the anatomical tissue;
   at least one ring electrode coupled to the lead and operable to deliver the therapy to a second portion of the anatomical tissue;
   a switch operable to electrically couple the at least one conductor to the at least one tip electrode or to the at least one ring electrode; and
   at least one control system operable to activate the switch to electrically couple the at least one conductor to the at least one tip electrode in a first operational state or to electrically couple the at least one conductor to the at least one ring electrode in a second operational state based on an external field.

15. The device of claim 14, wherein the external field comprises a magnetic or electric field generated during a magnetic resonance imaging (MRI) scan.

16. The device of claim 14, wherein the therapy device is an implantable pulse generator (IPG) and the lead is an IPG stimulation lead.

17. The device of claim 14, wherein the at least one conductor further comprises:
   a pacing conductor that receives the therapy from the therapy device and delivers the therapy to either the at least one tip electrode or the at least one ring electrode depending upon the first operational state or the second operational state; and
   a sensing conductor in electrical communication with the at least one ring electrode to receive a signal indicative of electrical activity at the second portion of the anatomical tissue and in electrical communication with the therapy device to conduct the signal to the therapy device.

18. The device of claim 17, wherein the control system further comprises:
   at least one sensor responsive to the external field to generate a signal; and
   at least one controller in communication with the at least one sensor to receive the signal and in electrical communication with the switch to activate the switch such that the switch electrically couples the pacing conductor to either the at least one ring electrode or the at least one tip electrode based on the signal from the at least one sensor.

19. The device of claim 18, wherein the therapy device delivers the therapy at a first voltage if the therapy device is in electrical communication with the at least one tip electrode and delivers the therapy at a second voltage if the therapy device is in electrical communication with the at least one ring electrode, the second voltage being greater than the first voltage.

20. The device of claim 18, wherein the at least one sensor further comprises:
   a first sensor disposed in the therapy device and responsive to the external field to generate a first signal;
   a second sensor disposed in the lead and responsive to the external field to generate a second signal; and
   wherein the at least one controller receives the first signal and second signal and based on the first signal and second signal determines if the external field is present and outputs error data if the first signal is not about equal to the second signal.

21. The device of claim 20, wherein the at least one controller further comprises:
   a first controller disposed in the therapy device and in communication with the at least the first sensor to receive the first signal and to generate the therapy;
   a second controller disposed in the lead and in communication with the second sensor to receive the second signal and in communication the first controller to receive the first signal, the second controller operable to activate the switch based on the first signal, the second signal or a combination thereof.

22. A method of controlling a cardiac lead implanted in an anatomical structure during the presence of an external field comprising:
   providing a lead having at least one conductor passing through the lead, at least one first electrode operable to be in electrical communication with the at least one conductor to deliver a therapy to a first portion of an anatomical tissue associated with the anatomical structure and at least one second electrode operable to be in electrical communication with the at least one conductor to deliver a therapy to a second portion of the anatomical tissue;
   determining whether the external field is present;
   electrically coupling the at least one first electrode with the at least one conductor to deliver the therapy if the external field is not present; and
   electrically coupling the at least one second electrode with the at least one conductor to deliver the therapy if the external field is present.

23. The method of claim 22, further comprising:
   providing a therapy device that generates the therapy;
   providing a programmer operable to program the therapy device to generate the therapy; and
   programming the therapy device to generate the therapy.

24. The method of claim 23, wherein determining whether the external field is present further comprises:
   sensing the external field by a sensor disposed in the therapy device;
   sensing the external field by a sensor disposed in the lead;
   receiving a signal from the programmer that indicates that the external field is present; or
   combinations thereof.

25. The method of claim 23, wherein electrically coupling the at least one first electrode and the at least one second electrode further comprises:
   changing the therapy generated by the therapy device to a first voltage if the at least one first electrode is electrically coupled with the at least one conductor;
   changing the therapy generated by the therapy device to a second voltage if the at least one second electrode is electrically coupled with the at least one conductor, with the second voltage being greater than the first voltage.

* * * * *